United States Patent
Augustine et al.

(10) Patent No.: US 7,851,729 B2
(45) Date of Patent: Dec. 14, 2010

(54) ELECTRIC WARMING BLANKET HAVING OPTIMIZED TEMPERATURE ZONES

(75) Inventors: Scott D. Augustine, Bloomington, MN (US); Randall C. Arnold, Minnetonka, MN (US); Rudolf A. Deibel, Eden Prairie, MN (US); Scott A. Entenman, St. Paul, MN (US); Keith J. Leland, Medina, MN (US); Thomas F. Neils, Minneapolis, MN (US)

(73) Assignee: Augustine Temperature Management LLC, Eden Prairie, MN (US)

( * ) Notice: Subject to any disclaimer, the term of this patent is extended or adjusted under 35 U.S.C. 154(b) by 0 days.

(21) Appl. No.: 11/537,173

(22) Filed: Sep. 29, 2006

(65) Prior Publication Data

US 2007/0068930 A1 Mar. 29, 2007

Related U.S. Application Data

(60) Provisional application No. 60/722,106, filed on Sep. 29, 2005, provisional application No. 60/722,246, filed on Sep. 29, 2005.

(51) Int. Cl.
*H05B 3/34* (2006.01)
(52) U.S. Cl. .............. 219/549; 219/212; 219/217; 219/528; 219/545; 219/548
(58) Field of Classification Search .......... 219/202, 219/211, 212, 217, 525, 527, 528, 529, 538, 219/544, 545, 548, 549; 428/214, 220, 428; 604/500; 607/108
See application file for complete search history.

(56) References Cited

U.S. PATENT DOCUMENTS

| | | | |
|---|---|---|---|
| 3,808,403 A | 4/1974 | Kanaya et al. | |
| 3,839,621 A | 10/1974 | Hariu | |
| 3,900,654 A | * 8/1975 | Stinger | 428/214 |
| 3,936,661 A | 2/1976 | Furuishi et al. | |
| 4,061,898 A | * 12/1977 | Murray et al. | 219/211 |
| 4,149,066 A | 4/1979 | Niibe | |

(Continued)

FOREIGN PATENT DOCUMENTS

GB 586745 3/1947

(Continued)

OTHER PUBLICATIONS

EeonTexTM Conductive Textiles, Product Details, www.eeonyx.com/prodte.html, Sep. 19, 2006, pp. 1-5.

(Continued)

*Primary Examiner*—Tu B Hoang
*Assistant Examiner*—Vinod D Patel
(74) *Attorney, Agent, or Firm*—Fredrikson & Byron, P.A.

(57) ABSTRACT

An electric heating blanket system includes a flexible sheet-like heating element having a substantially uniform watt density output across a surface area thereof, when the heating element is electrically powered. A temperature sensor is coupled to the heating element at a location where the heating element will be in conductive contact with a body when the blanket is draped over the body. The system further includes a temperature controller coupled to the temperature sensor, and an electric power source coupled to the heating element and to the temperature controller, the power source being controlled to provide the watt density output for the heating element according to a temperature sensed by the sensor.

7 Claims, 5 Drawing Sheets

U.S. PATENT DOCUMENTS

| | | | |
|---|---|---|---|
| 4,479,795 A * | 10/1984 | Mustacich et al. | 604/500 |
| 4,534,886 A | 8/1985 | Kraus et al. | |
| 4,626,664 A | 12/1986 | Grise | |
| 4,719,335 A | 1/1988 | Batliwalla et al. | |
| 4,764,665 A | 8/1988 | Orban et al. | |
| 4,798,936 A | 1/1989 | Johnson, Sr. | |
| 4,912,306 A | 3/1990 | Grise et al. | |
| 5,008,515 A * | 4/1991 | McCormack | 219/212 |
| 5,010,233 A | 4/1991 | Henschen et al. | |
| 5,023,433 A | 6/1991 | Gordon | |
| 5,380,580 A | 1/1995 | Rogers et al. | |
| 5,422,462 A * | 6/1995 | Kishimoto | 219/545 |
| 5,443,056 A | 8/1995 | Smith et al. | |
| 5,773,275 A | 6/1998 | Anderson et al. | |
| 5,817,145 A | 10/1998 | Augustine et al. | |
| 5,824,996 A | 10/1998 | Kochman et al. | |
| 5,928,274 A | 7/1999 | Augustine | |
| 5,964,792 A | 10/1999 | Augustine | |
| 5,974,605 A | 11/1999 | Dickerhoff et al. | |
| 5,986,243 A | 11/1999 | Campf | |
| 6,078,026 A | 6/2000 | West | |
| 6,093,910 A | 7/2000 | McClintock et al. | |
| 6,172,344 B1 * | 1/2001 | Gordon et al. | 219/529 |
| 6,184,496 B1 | 2/2001 | Pearce | |
| 6,235,049 B1 * | 5/2001 | Nazerian | 607/108 |
| 6,373,034 B1 | 4/2002 | Rock et al. | |
| 6,403,935 B2 | 6/2002 | Kochman et al. | |
| 6,483,087 B2 | 11/2002 | Gardner et al. | |
| 6,582,456 B1 | 6/2003 | Hand et al. | |
| 6,770,848 B2 | 8/2004 | Haas et al. | |
| 6,770,854 B1 | 8/2004 | Keane | |
| 6,839,922 B1 | 1/2005 | Foggett et al. | |
| 6,933,469 B2 | 8/2005 | Ellis et al. | |
| 6,974,935 B2 | 12/2005 | O'Grady | |
| 7,022,950 B2 | 4/2006 | Haas et al. | |
| 7,053,344 B1 * | 5/2006 | Surjan et al. | 219/549 |
| 2002/0005398 A1 | 1/2002 | Gillner et al. | |
| 2002/0117495 A1 | 8/2002 | Kochman et al. | |
| 2005/0016982 A1 | 1/2005 | Campf et al. | |

OTHER PUBLICATIONS

U.S. Appl. No. 11/537,179, Office Action dated Aug. 16, 2007, 6 pages.
U.S. Appl. No. 11/537,179, Office Action dated Dec. 31, 2007, 18 pages.
U.S. Appl. No. 11/537,179, Final Office Action dated Aug. 7, 2008, 15 pages.
U.S. Appl. No. 11/537,189, Office Action dated Aug. 16, 2007, 5 pages.
U.S. Appl. No. 11/537,189, Office Action dated Dec. 28, 2007, 12 pages.
U.S. Appl. No. 11/537,189, Final Office Action dated Aug. 6, 2008, 12 pages.
U.S. Appl. No. 11/537,212, Office Action dated Feb. 23, 2007, 5 pages.
U.S. Appl. No. 11/537,212, Office Action dated Jul. 18, 2007, 7 pages.
U.S. Appl. No. 11/537,212, Final Office Action dated Mar. 17, 2008, 8 pages.
U.S. Appl. No. 111537,212, Notice of Allowance dated Sep. 26, 2008, 6 pages.
U.S. Appl. No. 111537,222, Office Action dated Feb. 23, 2007, 8 pages.
U.S. Appl. No. 11/537,222, Office Action dated Jul. 18, 2007, 6 pages.
U.S. Appl. No. 11/537,222, Final Office Action dated May 1, 2008, 7 pages.
PCT Application No. PCT/US2006/038232, International Search Report and Written Opinion, dated Jan. 23, 2007, 11 pages.
PCT Application No. PCT/US2006/038231, International Search Report and Wirtten Opinion, dated Aug. 20, 2007, 8 pages.
U.S. Appl. No. 11/537,179, Office Action, dated May 27, 2009, 17 pages.
U.S. Appl. No. 11/537,189, Office Action, dated Apr. 28, 2009, 14 pages.
U.S. Appl. No. 11/537,222, Final Office Action, dated Nov. 12, 2008, 7 pages.
U.S. Appl. No. 11/537,179, Office Action, dated Nov. 18, 2009, 11 pages.
U.S. Appl. No. 11/537,189, Final Office Action, dated Oct. 27, 2009, 20 pages.

* cited by examiner

ELECTRIC WARMING BLANKET HAVING OPTIMIZED TEMPERATURE ZONES

PRIORITY CLAIM

The present application claims priority to provisional application Ser. No. 60/722,106 entitled: ELECTRIC WARMING BLANKET INCLUDING TEMPERATURE ZONES AUTOMATICALLY OPTIMIZED, and to provisional application Ser. No. 60/722,246, entitled: HEATING BLANKET, both of which were filed on Sep. 29, 2005, and both of which are incorporated by reference in their entireties herein.

RELATED APPLICATIONS

The present application is related to the following commonly assigned utility patent applications, all of which are filed concurrently herewith and all of which are hereby incorporated by reference in their entireties: A) NOVEL DESIGNS FOR HEATING BLANKETS AND PADS, Practitioner Ser. No. 11/537,179B) TEMPERATURE SENSOR ASSEMBLIES FOR AN ELECTRIC WARMING BLANKET, Practitioner Ser. No. 11/537,189; C) FLEXIBLE HEATING ELEMENT CONSTRUCTION, Practitioner Ser. No. 11/537,199; D) BUS BAR ATTACHMENTS FOR FLEXIBLE HEATING ELEMENTS, Practitioner Ser. No. 11/537,212; and E) BUS BAR INTERFACES FOR FLEXIBLE HEATING ELEMENTS, Practitioner Ser. No. 11/537,222.

TECHNICAL FIELD

The present invention is related to heating or warming blankets and more particularly to heating blankets including electrical heating elements.

BACKGROUND

It is well established that surgical patients under anesthesia become poikilothermic. This means that the patients lose their ability to control their body temperature and will take on or lose heat depending on the temperature of the environment. Since modern operating rooms are all air conditioned to a relatively low temperature for surgeon comfort, the majority of patients undergoing general anesthesia will lose heat and become clinically hypothermic if not warmed.

Over the past 15 years, forced-air warming (FAW) has become the "standard of care" for preventing and treating the hypothermia caused by anesthesia and surgery. FAW consists of a large heater/blower attached by a hose to an inflatable air blanket. The warm air is distributed over the patient within the chambers of the blanket and then is exhausted onto the patient through holes in the bottom surface of the blanket.

Although FAW is clinically effective, it suffers from several problems including: a relatively high price; air blowing in the operating room, which can be noisy and can potentially contaminate the surgical field; and bulkiness, which, at times, may obscure the view of the surgeon. Moreover, the low specific heat of air and the rapid loss of heat from air requires that the temperature of the air, as it leaves the hose, be dangerously high—in some products as high as 45° C. This poses significant dangers for the patient. Second and third degree burns have occurred both because of contact between the hose and the patient's skin, and by blowing hot air directly from the hose onto the skin without connecting a blanket to the hose. This condition is common enough to have its own name—"hosing." The manufacturers of forced air warming equipment actively warn their users against hosing and the risks it poses to the patient.

To overcome the aforementioned problems with FAW, several companies have developed electric warming blankets. However, these electric blankets have a number of inadequacies, examples of which include, a stiffness prohibiting a draping of the blankets over a patient that results in less than optimal conductive heat transfer to the patient, and a non-uniform watt density output across a surface area of the blankets.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

DETAILED DESCRIPTION

The following detailed description is exemplary in nature and is not intended to limit the scope, applicability, or configuration of the invention in any way. Rather, the following description provides practical illustrations for implementing exemplary embodiments of the present invention. Examples of constructions, materials, dimensions, and manufacturing processes are provided for selected elements, and all other elements employ that which is known to those of skill in the field of the invention. Those skilled in the art will recognize that many of the examples provided have suitable alternatives that can be utilized. The term 'blanket', used to describe embodiments of the present invention, may be considered to encompass heating blankets and pads.

Figure 1B:
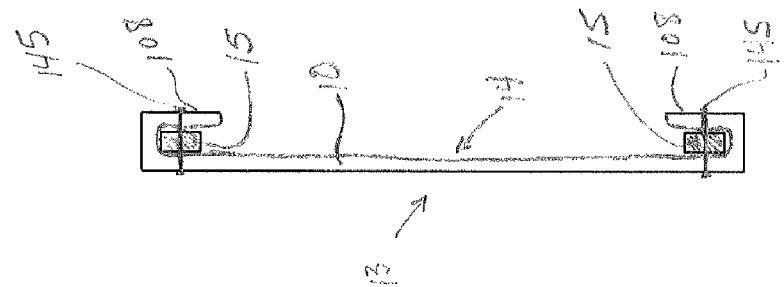
FIG. 1B is an end view of the subassembly shown in FIG. 1A.
Figure 1A:
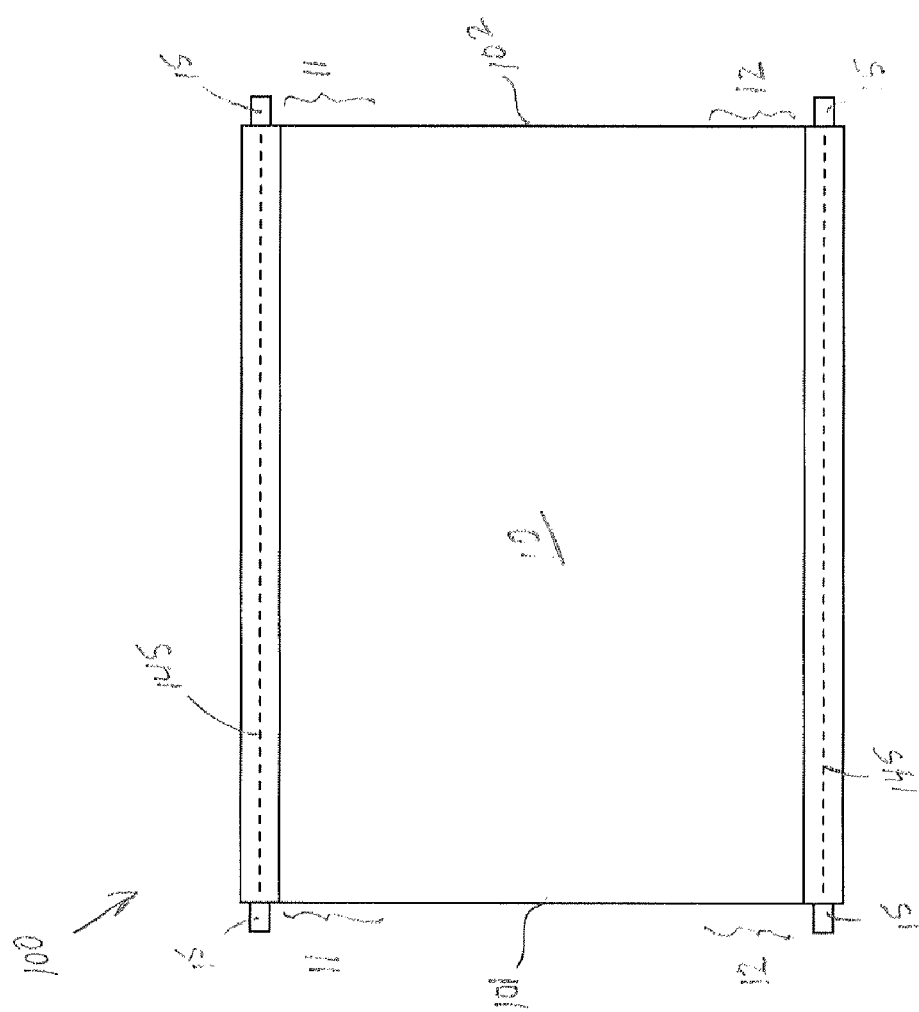
FIG. 1A is a plan view of a flexible heating blanket subassembly for a heating blanket, according to some embodiments of the present invention.

FIG. 1A is a plan view of a flexible heating blanket subassembly 100, according to some embodiments of the present invention; and FIG. 1B is an end view of the subassembly shown in FIG. 1A. FIG. 1A illustrates a flexible sheet-like heating element 10 of subassembly 100 including a first end 101, a second end 102, a first lateral portion 11 extending between ends 101, 102, and a second lateral portion 12, opposite first lateral portion 11, also extending between ends 101, 102. According to preferred embodiments of the present invention, heating element 10 comprises a conductive fabric or a fabric incorporating closely spaced conductive elements such that heating element 10 has a substantially uniform watt density output, preferably less than approximately 0.5 watts/ sq. inch, and more preferably between approximately 0.2 and approximately 0.4 watts/sq. inch, across a surface area, of one or both sides 13, 14, the surface area including and extending between lateral portions 11, 12 of heating element 10. Some examples of conductive fabrics which may be employed by embodiments of the present invention include, without limitation, carbon fiber fabrics, fabrics made from carbonized fibers, woven or non-woven non-conductive substrates coated with a conductive material, for example, polypyrrole, carbonized ink, or metalized ink. Of course, the substantially uniform watt density output is based on the heating element having a conductivity or resistance that is substantially uniform over the area of the heating element 10.

FIG. 1A further illustrates subassembly 100 including two bus bars 15 coupled to heating element 10 for powering element 10; each bar 15 is shown extending alongside opposing lateral portions 11, 12, between first and second ends 101, 102. With reference to FIG. 1B, according to some embodiments, bus bars 15 are coupled to heating element 10 within folds of opposing wrapped perimeter edges 108 of heating element 10 by at least one row of stitching 145, for example, formed with conductive thread such as silver-coated polyester, extending through edges 108 of heating element 10, bars 15, and again through heating element 10 on opposite side of bars 15. According to an exemplary embodiment, bars 15 are comprised of flattened tubes of braided wires, such as are known to those skilled in the art, and may thus accommodate the thread extending therethrough, passing through openings between the braided wires thereof. In addition such bars are flexible to enhance the flexibility of blanket subassembly 100. According to alternate embodiments, bus bars 15 can be a conductive foil or wire, flattened braided wires not formed in tubes, an embroidery of conductive thread or a printing of conductive ink.

According to an exemplary embodiment, a conductive fabric for heating element 10 comprises a non-woven polyester having a basis weight of approximately 130 g/m$^2$ and being 100% coated with polypyrrole (available from Eeonyx Inc., Pinole, Calif.); the coated fabric has an average resistance, for example, determined with a four point probe measurement, of approximately 15-20 ohms per square, at about 48 volts, which is suitable to produce the preferred watt density of 0.2 to 0.4 watts/sq. in. for surface areas of heating element 10 having a width, between bus bars 15, in the neighborhood of about 20 inches. Such a width is suitable for a lower body heating blanket, an exemplary embodiment of which will be described below. A resistance of such a conductive fabric may be tailored for different widths between bus bars (wider requiring a lower resistance and narrower requiring a higher resistance) by increasing or decreasing a surface area of the fabric that can receive the conductive coating, for example by increasing or decreasing the basis weight of the fabric.

Figure 1C:
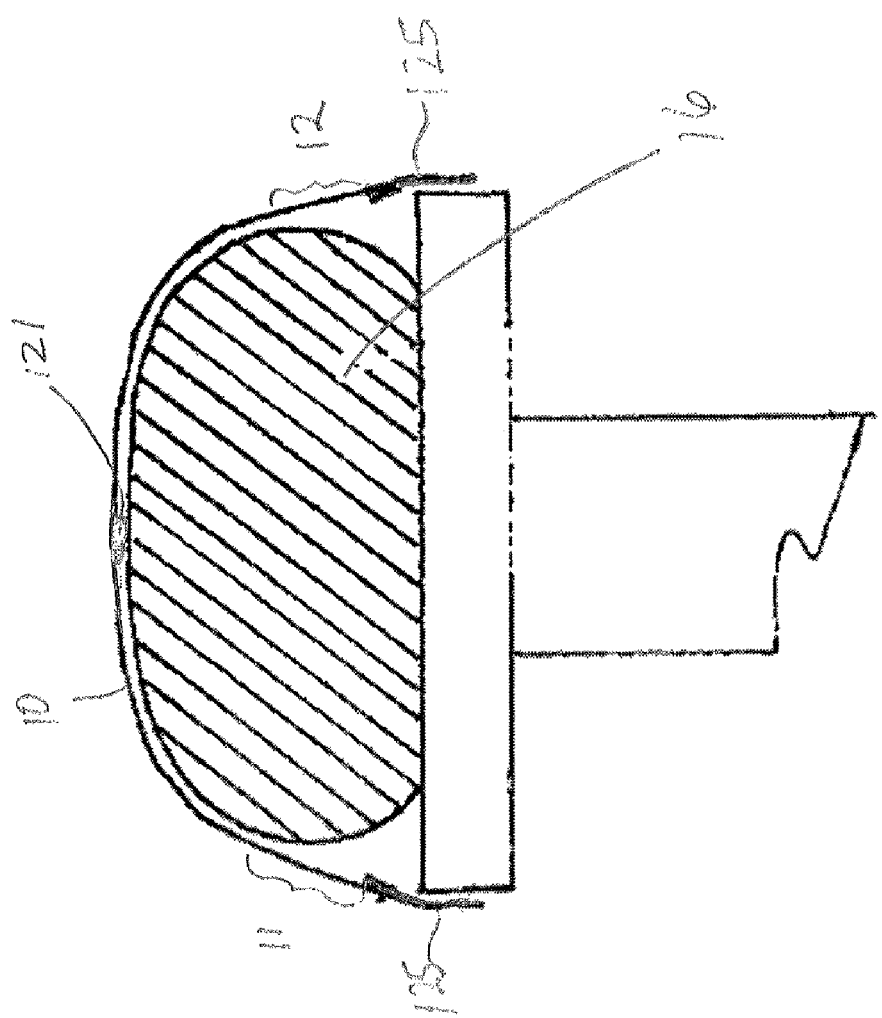
FIG. 1C is a schematic showing a blanket including the subassembly of FIG. 1A draped over a body.

A flexibility of blanket subassembly 100, provided primarily by flexible heating element 10, and optionally enhanced by the incorporation of flexible bus bars, allows blanket subassembly 100 to conform to the contours of a body, for example, all or a portion of a patient undergoing surgery, rather than simply bridging across high spots of the body; such conformance may optimize a conductive heat transfer from element 10 to a surface of the body. However, as illustrated in FIG. 1C, heating element 10 may be draped over a body 16 such that lateral portions 11,12 do not contact side surfaces of body 16; the mechanism of heat transfer between portions 11, 12 and body 16, as illustrated in FIG. 1D, is primarily radiant with some convection.

The uniform watt-density output across the surface areas of preferred embodiments of heating element 10 translates into a uniform heating of the surface areas, but not necessarily a uniform temperature. At locations of heating element 10 which are in conductive contact with a body acting as a heat sink, for example, body 16, the heat is efficiently drawn away from heating element 10 and into the body, for example by blood flow, while at those locations where element 10 does not come into conductive contact with the body, for example lateral portions 11, 12 as illustrated in FIG. 1C, an insulating air gap exists between the body and those portions, so that the heat is not drawn off those portions as easily. Therefore, those portions of heating element 10 not in conductive contact with the body will gain in temperature, since heat is not transferred as efficiently from these portions as from those in conductive contact with the body. The 'non-contacting' portions will reach a higher equilibrium temperature than that of the 'contacting' portions, when the radiant and convective heat loss equal the constant heat production through heating element 10. Although radiant and convective heat transfer are more efficient at higher heater temperatures, the laws of thermodynamics dictate that as long as there is a uniform watt-density of heat production, even at the higher temperature, the radiant and convective heat transfer from a blanket of this construction will result in a lower heat flux to the skin than the heat flux caused by the conductive heat transfer at the lower temperature. Even though the temperature is higher, the watt-density is uniform and, since the radiant and convective heat transfer are less efficient than conductive heat transfer, the 'non-contacting' portions must have a lower heat flux. Therefore, by controlling the 'contacting' portions to a safe temperature, for example, via a temperature sensor 121 coupled to heating element 10 in a location where element 10 will be in conductive contact with the body, as illustrated in FIG. 1C, the 'non-contacting' portions, for example, lateral portions 11, 12, will also be operating at a safe temperature because of the less efficient radiant and convective heat transfer. According to preferred embodiments, heating element 10 comprises a conductive fabric having a relatively small thermal mass so that when a portion of the heater that is operating at the higher temperature is touched, suddenly converting a 'non-contacting' portion into a 'contacting' portion, that portion will cool almost instantly to the safe operating temperature.

According to embodiments of the present invention, zones of heating element 10 may be differentiated according to whether or not portions of element 10 are in conductive contact with a body, for example, a patient undergoing surgery. In the case of conductive heating, gentle external pressure may be applied to a heating blanket including heating element 10, which pressure forces heating element 10 into better conductive contact with the patient to improve heat transfer. However, if excessive pressure is applied the blood flow to that skin may be reduced at the same time that the heat transfer is improved and this combination of heat and pressure to the skin can be dangerous. It is well known that patients with poor perfusion should not have prolonged contact with conductive heat in excess of approximately 42° C. 42° C. has been shown in several studies to be the highest skin temperature, which cannot cause thermal damage to normally perfused skin, even with prolonged exposure. (Stoll & Greene, Relationship between pain and tissue damage due to thermal radiation. J. Applied Physiology 14(3):373-382. 1959. and Moritz and Henriques, Studies of thermal injury: The relative importance of time and surface temperature in the causation of cutaneous burns Am. J. Pathology 23:695-720, 1947) Thus, according to certain embodiments of the present invention, the portion of heating element 10 that is in conductive contact with the patient is controlled to approximately 43° C. in order to achieve a temperature of about 41-42° C. on a surface a heating blanket cover that surrounds element 10, for example, a cover or shell 20 which will be described below in conjunction with FIG. 2B. With further reference to FIG. 1C, flaps 125 are shown extending laterally from either side of heating element 10 in order to enclose the sides of body 16 thereby preventing heat loss; according to preferred embodiments of the present invention, flaps 125 are not heated and thus provide no thermal injury risk to body if they were to be tucked beneath sides of body 16.

Figure 2A:
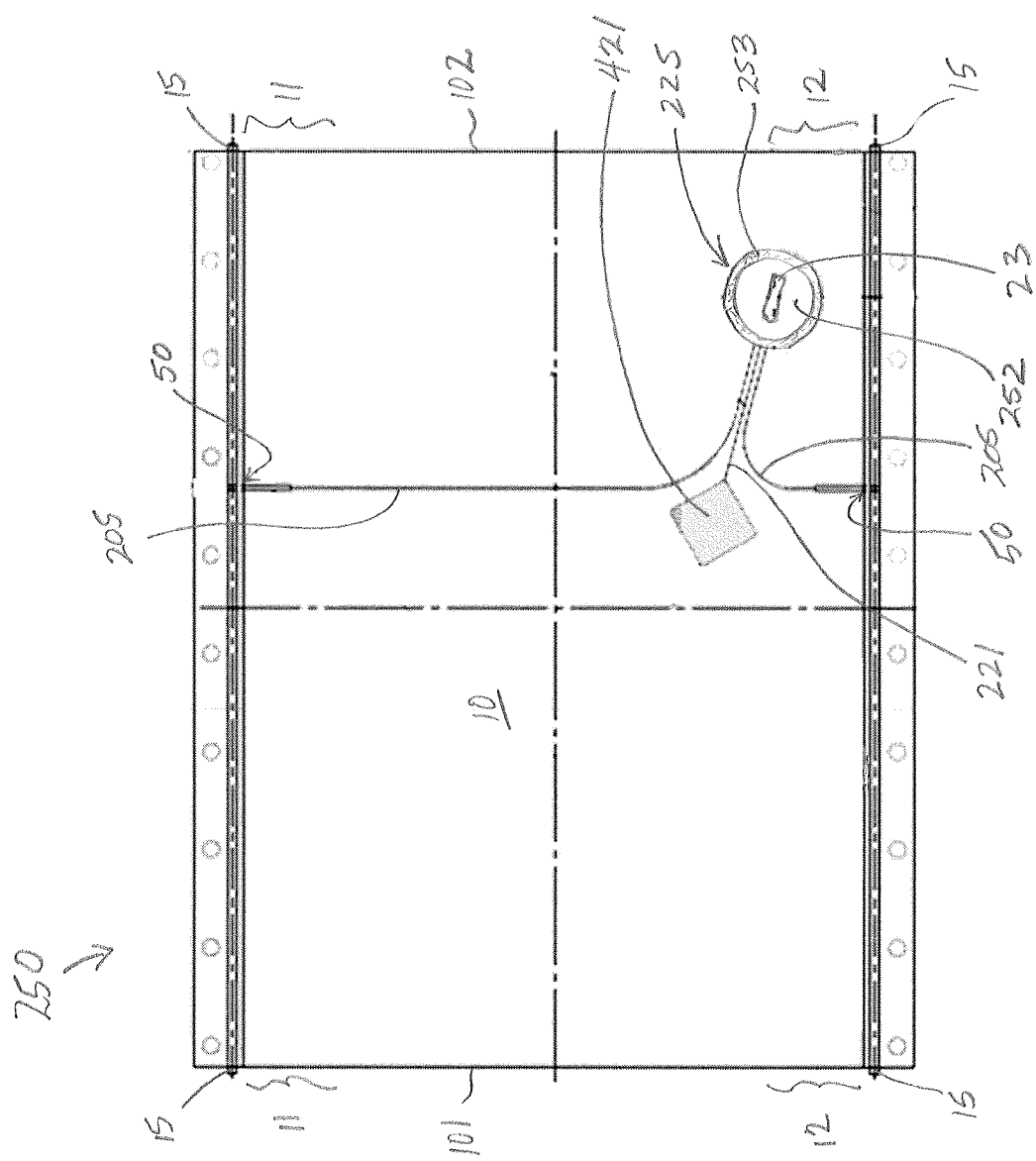
FIG. 2A is a top plan view, including a partial cut-away view, of a heating element assembly, according to some embodiments of the present invention, which may be incorporated in the blanket shown in FIG. 3A.
Figure 2B:
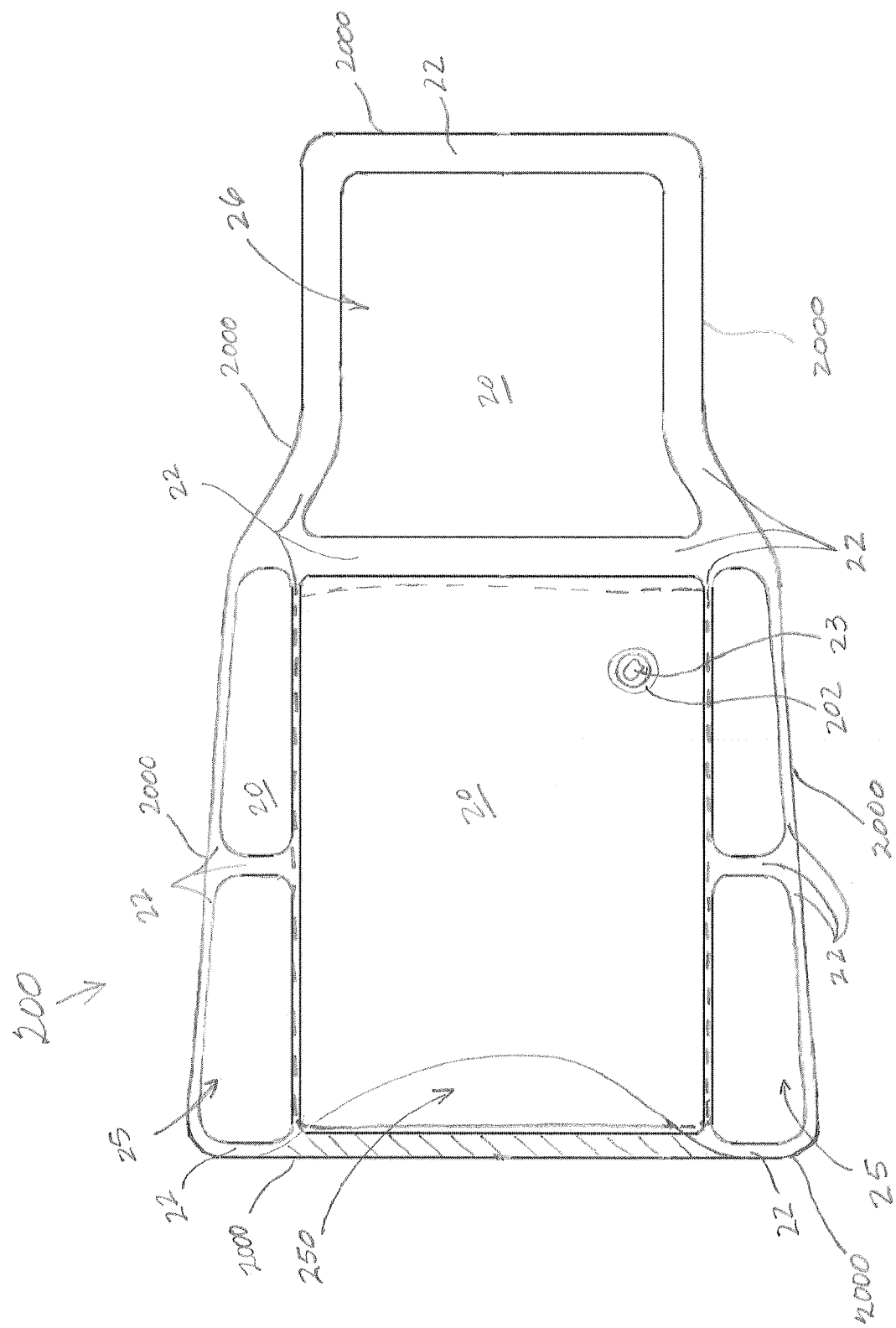
FIG. 2B is a top plan view, including a partial cut-away view, of a lower body heating blanket, according to some embodiments of the present invention.

FIG. 2A is a top plan view of a heating element assembly 250, according to some embodiments of the present invention, which may be incorporated by blanket 200, which is shown in FIG. 2B, and further described below. According to some embodiments, heating element 10 is overlaid on both sides with an electrically insulating layer, preferably formed of a flexible non-woven high loft fibrous material, for example, 1.5 OSY (ounces per square yard) nylon, and laminated to the sides with a hotmelt laminating adhesive. Other examples of suitable materials for the insulating layers include, without limitation, polymeric foam, a woven fabric, and a relatively thin plastic film. FIG. 2A illustrates junctions 50 coupling leads 205 to each bus bar 15, and another lead 221 coupled to and extending from a temperature sensor assembly 421, for example, including a surface mount chip thermistor, such as a Panasonic ERT-J 1VG103FA: 10K, 1% chip thermistor. Temperature sensor assembly 421 may be bonded to heating element with an adhesive, for example, hotmelt EVA. Leads 205, 221, being electrically isolated from heating element 10, for example, by one of the insulating layers described above, are shown extending over heating element 10 and into an electrical connector housing 225 containing a connector 23. According to certain embodiments, junction 50 includes a conductive insert, which has been secured to bus bar 15, for example, by inserting the insert through a side wall of bus bar 15 and into an inner diameter thereof, the bus bar 15 of the illustrated embodiment being formed by a braided wire tube so that an opening between the wires may be formed for access to the inner diameter. The insert may be secured to bus bar 15 by compressing tubular bus bar 15 around the insert and, further, by stitched coupling 145 that couples bus bar 15 to heating element 10. Lead 205 may be coupled to the insert, for example, by soldering, and an insulating tube, for example, a polymer shrink tube, may surround the coupling between lead 205 and the insert.

FIG. 2B is a top plan view, including a partial cut-away view, of a lower body heating blanket 200, according to some embodiments of the present invention, which may be used to keep a patient warm during surgery. FIG. 2B illustrates blanket 200 including heating element assembly 250 covered by flexible shell 20 (assembly 250 exposed in the partial cut-away and represented beneath shell 20 by dashed lines); shell 20 protects and isolates assembly 250 from an external environment of blanket 200 and may further protect a patient disposed beneath blanket 200 from electrical shock hazards. According to preferred embodiments of the present invention, shell 20 is waterproof to prevent fluids, for example, bodily fluids, IV fluids, or cleaning fluids, from contacting assembly 250, and may further include an anti-microbial element, for example, being a SILVERion™ antimicrobial fabric available from Domestic Fabrics Corporation.

Figure 2C:
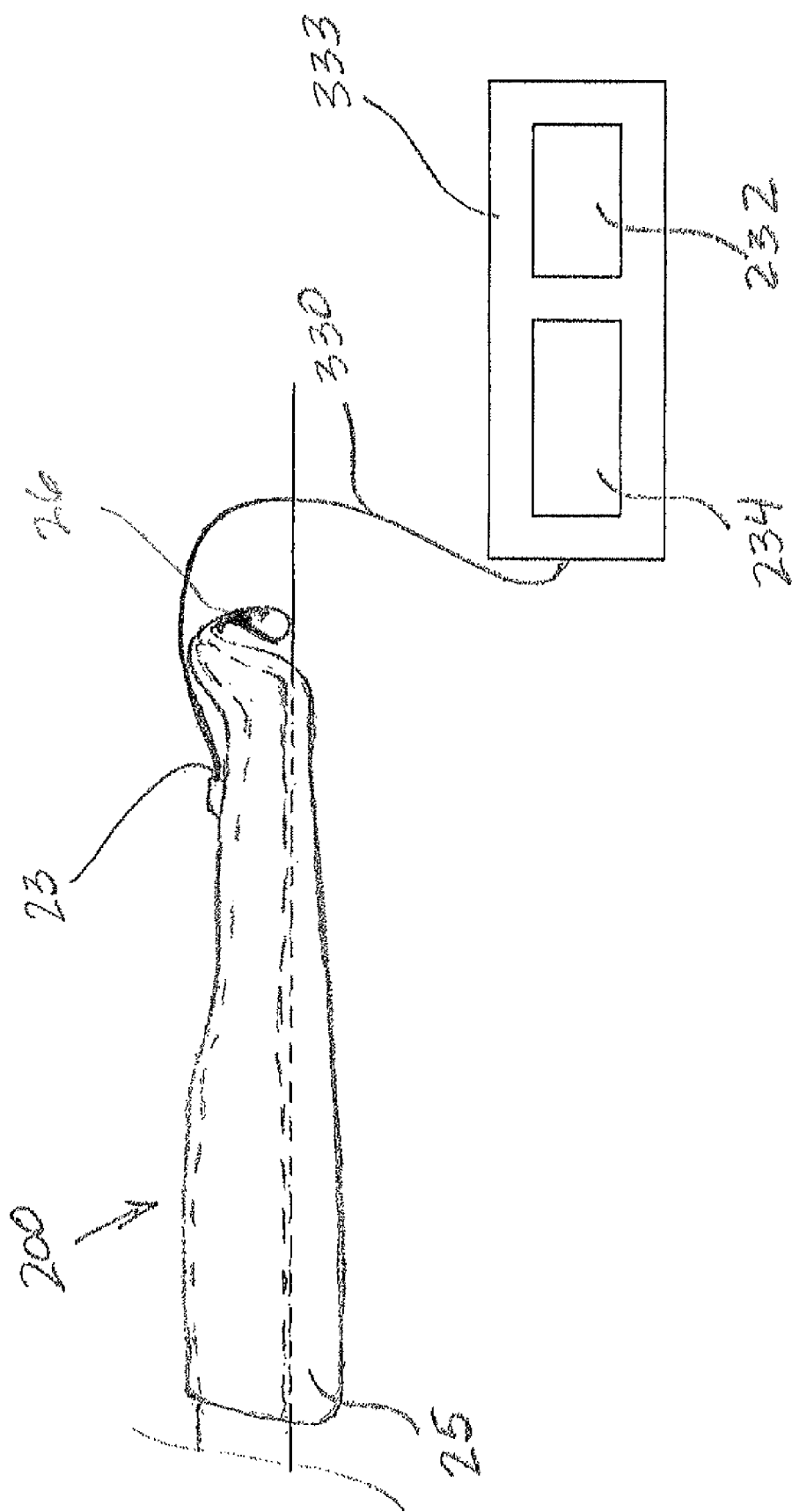
FIG. 2C is a schematic side view of the blanket of FIG. 2B draped over a lower body portion of a patient.

FIG. 2B further illustrates shell 20 forming side flaps 25 extending laterally from either side of heating element assembly 250 and a foot flap 26 extending longitudinally from assembly 250, all of the flaps being unheated. According to exemplary embodiments of the present invention, a length of assembly 250 is either approximately 28 inches or approximately 48 inches, the shorter length providing adequate coverage for smaller patients or a smaller portion of an average adult patient. FIG. 2C is a schematic side view of blanket 200 draped over a lower body portion of a patient. With reference to FIG. 2C it may be appreciated that flaps 25, extending down on either side of the patient, and foot flap 26, being folded under to form a pocket about the feet of the patient, together effectively enclose the lower body portion of the patient to prevent heat loss. It should be noted that blankets of the present invention can be of many shapes and sizes, and that blanket 200 is merely one example of a particular type of blanket that may incorporate heating elements of the present invention.

With further reference to FIG. 2C, it may also be appreciated that neither shell 20 (see FIG. 2B) nor electrical insulation layer overlaid on both sides of heating element 10 add appreciable stiffness to heating element 10 so that blanket 200 conforms nicely to the contour of the patient's lower body. Furthermore, with reference to FIGS. 2B-C, it may be appreciated that temperature sensor assembly 421 is located on assembly 250 so that, when blanket 200, including assembly 250, is draped over the lower body of the patient, the area of heating element 10 surrounding sensor assembly 421 will be in conductive contact with one of the legs of the patient in order to maintain a safe temperature distribution across element 10.

According to some embodiments of the present invention, shell 20 includes top and bottom sheets extending over either side of assembly 250; the two sheets of shell 20 are coupled together along a seal zone 22 that extends about a perimeter edge 2000 of blanket 200, and within perimeter edge 2000 to form zones, or pockets, where a gap exists between the two sheets. According to an exemplary embodiment of the present invention, shell 20 comprises a nylon fabric having an overlay of polyurethane coating to provide waterproofing; the coating is on at least an inner surface of each of the two sheets, further facilitating a heat seal between the two sheets, for example, along seal zone 22, according to preferred embodiments. It should be noted that, according to alternate embodiments of the present invention, a covering for heating assemblies, such as heating assembly 250, may be removable and, thus, include a reversible closure facilitating removal of a heating assembly therefrom and insertion of the same or another heating assembly therein.

Returning now to FIG. 2A, to be referenced in conjunction with FIGS. 2B-C, connector housing 225 and connector 23 will be described in greater detail. According to certain embodiments, housing 225 is an injection molded thermoplastic, for example, PVC, and may be coupled to assembly 250 by being stitched to heating element 10; FIG. 2A shows housing 225 including a flange 253 through which such stitching can extend. With reference to FIGS. 2B-C, it can be seen that connector 23 protrudes from shell 20 of blanket 200 so that an extension cable 330 may couple bus bars 15 to a power source 234, and temperature sensor assembly 421 to a temperature controller 232, both shown incorporated into a console 333. According to the illustrated embodiment, a seal 202 (FIG. 2B) may be formed, for example, by adhesive bonding and/or heat sealing, between an inner surface of shell 20 and a surface 252 of flange 253. According to an exemplary embodiment, wherein housing 225 is injection molded PVC and the inner surface of shell 20 is coated with polyurethane, a liquid adhesive, which bonds and heat seals to both PVC and polyurethane, is applied to surface 252 and allowed to cure prior to heat sealing shell 20 to surface 252. With further reference to FIG. 2C, it may be appreciated that the location of plug 23 is suitable to keep connector cord 330 well away from the surgical field.

In the foregoing detailed description, the invention has been described with reference to specific embodiments. However, it may be appreciated that various modifications and changes can be made without departing from the scope of the invention as set forth in the appended claims. Although embodiments of the invention are described in the context of an operating environment, it is contemplated that some embodiments of the invention may be used in other environments.

The invention claimed is:

1. A method of warming a patient during surgery, the method comprising:

providing a heating blanket comprising a flexible sheet-like heating element having generally uniform electrical resistance per unit area such that the heating element produces a substantially uniform watt density output across a surface area thereof when the heating element is electrically powered, the heating element including a first side and a second side opposite the first side, the first side having a temperature sensor coupled thereto at a location that defines a first temperature zone of the heating element;

placing the heating blanket over a patient, such that the second side of the heating element faces toward the patient, the first temperature zone of the heating element is in thermal conductive contact with the patient, and a second temperature zone of the heating element is alongside the patient but not in thermal conductive contact with the patient;

monitoring a temperature of the first temperature zone of the heating element, as sensed by the temperature sensor, after the blanket is placed over the patient; and controlling electric power to the heating element, according to the monitored temperature of the first temperature zone; and maintaining a first temperature of the first temperature zone only, the maintained first temperature being lower than a second temperature of the second temperature zone, after the blanket is placed over the patient.

2. The method of claim 1, further comprising extending, from the heating element, an unheated flap of the heating blanket along a side of the patient to enclose that side of the patient.

3. The method of claim 1, wherein the flexible sheet-like heating element comprises an electrically conductive fabric.

4. The method of claim 1, wherein the flexible sheet-like heating element comprises a nonconductive layer coated with an electrically conductive material.

5. The method of claim 4, wherein the nonconductive layer comprises woven polyester and the conductive material comprises polypyrrole.

6. The method of claim 1, wherein the flexible sheet-like heating element comprises a fabric incorporating closely spaced electrically conductive elements.

7. The method of claim 1, wherein the substantially uniform watt density is no greater than approximately 0.5 watts per square inch.

* * * * *